US011166756B2

(12) United States Patent
Ju et al.

(10) Patent No.: US 11,166,756 B2
(45) Date of Patent: Nov. 9, 2021

(54) PARTICULATE MATERIAL DELIVERY SYSTEM AND METHOD

(71) Applicant: JOY MEDICAL DEVICES CORPORATION, Kaohsiung (TW)

(72) Inventors: Chien-Ping Ju, Kansas City, MO (US); Jiin-Huey Chern Lin, Winnetka, IL (US); Yen-Chun Chen, Kaohsiung (TW); Bing-Chen Yang, Kaohsiung (TW); Kuan-Ting Chen, Kaohsiung (TW)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 175 days.

(21) Appl. No.: 16/479,999

(22) PCT Filed: Jan. 23, 2018

(86) PCT No.: PCT/US2018/014783
§ 371 (c)(1),
(2) Date: Jul. 23, 2019

(87) PCT Pub. No.: WO2018/140378
PCT Pub. Date: Aug. 2, 2018

(65) Prior Publication Data
US 2019/0365446 A1 Dec. 5, 2019

Related U.S. Application Data

(60) Provisional application No. 62/451,792, filed on Jan. 30, 2017.

(51) Int. Cl.
*A61B 17/88* (2006.01)
*A61F 2/46* (2006.01)
(Continued)

(52) U.S. Cl.
CPC ...... *A61B 17/8822* (2013.01); *A61B 17/8816* (2013.01); *A61F 2/4601* (2013.01);
(Continued)

(58) Field of Classification Search
CPC ............ A61B 17/8802; A61B 17/8805; A61B 17/8816; A61B 17/8822
See application file for complete search history.

(56) References Cited

U.S. PATENT DOCUMENTS

| 4,950,243 A | 8/1990 | Estruch |
| 2005/0070912 A1* | 3/2005 | Voellmicke ........ A61B 17/8816 606/92 |

(Continued)

FOREIGN PATENT DOCUMENTS

| EP | 1303236 A2 | 4/2003 |
| KR | 1020080021672 A | 3/2008 |
| WO | WO2016-010836 A1 | 1/2016 |

OTHER PUBLICATIONS

Extended European Search report cited in European Appln. No. 18744678.6 dated Dec. 9, 2019.

*Primary Examiner* — Kevin T Truong
*Assistant Examiner* — Lisa Nguyen
(74) *Attorney, Agent, or Firm* — Bacon & Thomas, PLLC (57) ABSTRACT

In order to deliver porous particulate material into a cavity via a thin tube without substantially crushing the porous particulate material, a two-step process and an apparatus for use therein are provided. The two-step process involves inserting a first rod into the thin tube to push the porous particulate material therein; removing the first rod from the tube; and (a) inserting a second rod into the thin tube, or (b) joining a second rod with the first rod, and inserting the joined first rod and second rod, to push the porous particulate material which remains in the thin tube. In (a), the first rod has a cross sectional area significantly smaller than that (Continued)

of the thin tube, and the second rod has a cross sectional area which is about equal to that of the thin tube. In (b), each of the first rod and the second rod has a cross sectional area about half of the thin tube.

5 Claims, 6 Drawing Sheets

(51) Int. Cl.
    *A61F 2/28*         (2006.01)
    *A61F 2/30*         (2006.01)

(52) U.S. Cl.
    CPC ... *A61B 17/8811* (2013.01); *A61F 2002/2835* (2013.01); *A61F 2002/30784* (2013.01)

(56) References Cited

U.S. PATENT DOCUMENTS

| | | |
|---|---|---|
| 2007/0093759 A1 | 4/2007 | Sickler |
| 2007/0233146 A1 | 10/2007 | Henniges et al. |
| 2010/0106133 A1* | 4/2010 | Simonton ......... A61M 37/0069 604/506 |
| 2010/0114075 A1* | 5/2010 | Simonton ............ A61M 25/00 604/892.1 |
| 2015/0011946 A1 | 1/2015 | Masson et al. |
| 2015/0164562 A1 | 6/2015 | Anderson et al. |
| 2015/0182669 A1 | 7/2015 | Walsh |
| 2015/0319917 A1 | 11/2015 | Henry et al. |
| 2016/0192973 A1* | 7/2016 | Shimko ................ A61F 2/4601 141/2 |

* cited by examiner

PARTICULATE MATERIAL DELIVERY SYSTEM AND METHOD

FIELD OF THE INVENTION

The present invention is related to a technique for delivering particulate material such as granules and pellets, in particular porous particulate material, into a bone cavity, for enhancing bone ingrowth. Alternatively, liquid such as blood might be added to the particulate material prior to the delivery.

BACKGROUND OF THE INVENTION

The conventional syringe is designed for delivering liquid, or sometimes paste. When the conventional syringe is used to deliver granules, in particular fragile porous granules, into a bone cavity, for enhancing bone ingrowth, the frictions created between the surfaces of the granules themselves and between the surfaces of the granules and the inner surface of a barrel of the syringe and a thin tube connecting the barrel to the bone cavity are often too large to successfully complete the delivery, especially when the granules are porous granules which would be crushed by the friction.

WO 2016/010836 A discloses a new measure to solve the aforesaid delivery puzzle, wherein a particulate material delivery system is provided comprising a plunger and a divided tube, the divided tube has two or more partial shells which are suitable to be coupled to each other, so that a longitudinal channel is formed in the divided tube, each of the partial shells is able to move longitudinally in relation to the other, and the plunger is able to be inserted into the longitudinal channel. The two or more partial shells are coupled to each other, and particulate material is filled in the longitudinal channel. The particulate material is held steady by the plunger while the two or more partial shells of the divided tube are withdrawn one at a time, so that the particulate material originally in the divided tube is exposed gradually from a distal end thereof, and thus falls from the divided tube. Indeed, the measure provided in WO 2016/010836 A is able to deliver the particulate material with a minimum possible friction being created, and to successfully deliver porous particulate material without crushing it. However, a more convenient measure is still possible to achieve the same goals.

SUMMARY OF THE INVENTION

The gist of the present invention is to provide a new measure to deliver particulate material, in particular porous particulate material, such as porous granules and porous pellets formed by bone cement. The measure provided in the present invention is able to deliver the particulate material with less friction being created, and to deliver more porous particulate material with less porous particulate material being crushed.

An apparatus for delivering particulate material constructed according to the present invention comprises the features recited in claim 1 and its dependent claims.

A system for delivering particulate material constructed according to the present invention comprises the features recited in claim 2 and its dependent claims.

The present invention further provides a method of delivering particulate material into a space comprising features recited in claim 4 and its dependent claims.

As desired, liquid such as blood might be added to the particulate material prior to the delivery.

Preferred embodiments of the present invention include (but not limited to) those recited in the accompanying claims.

DETAILED DESCRIPTION OF THE INVENTION

Figure 1:
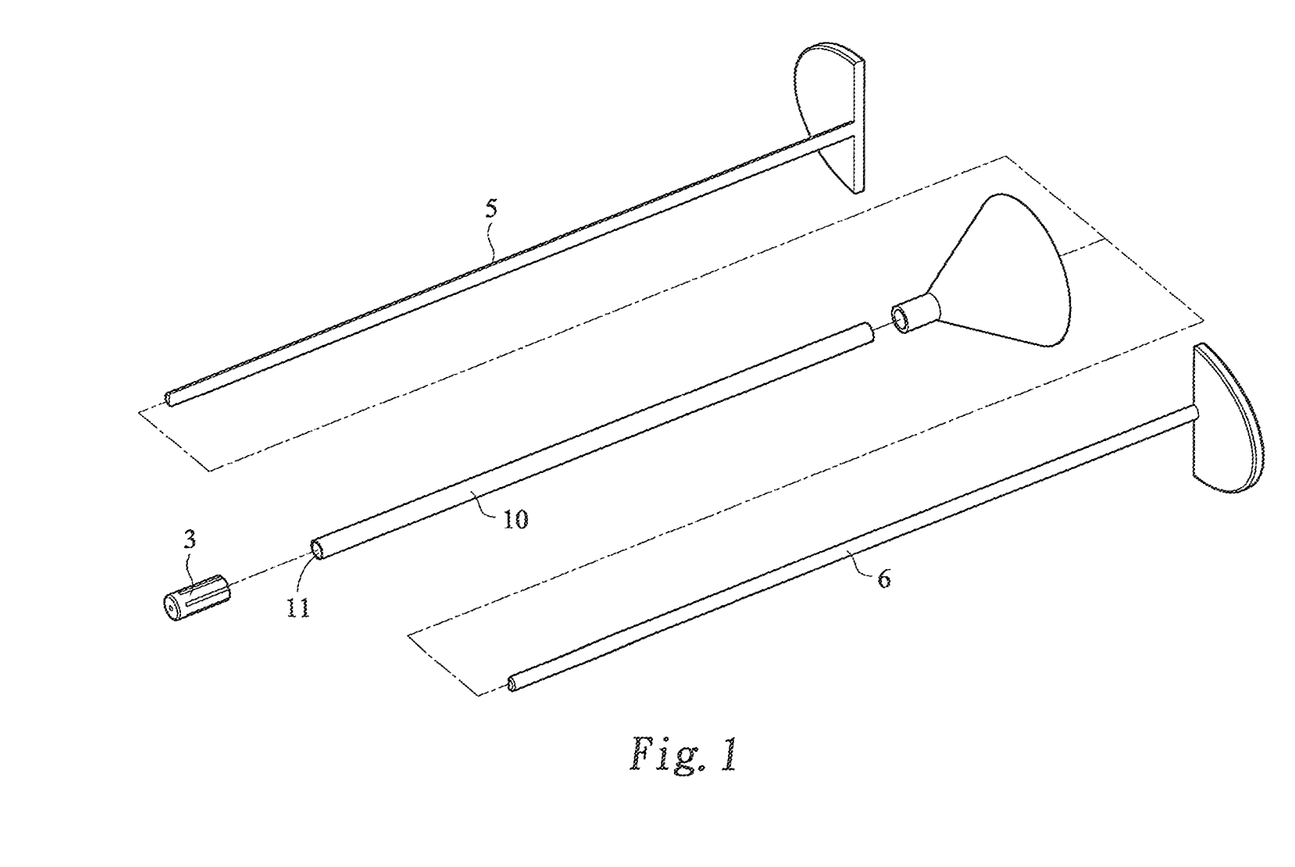
FIG. 1 is a perspective view showing a granule delivery system (hereinafter abbreviated as GDS) constructed according to a first preferred embodiment of the present invention.
Figure 2:
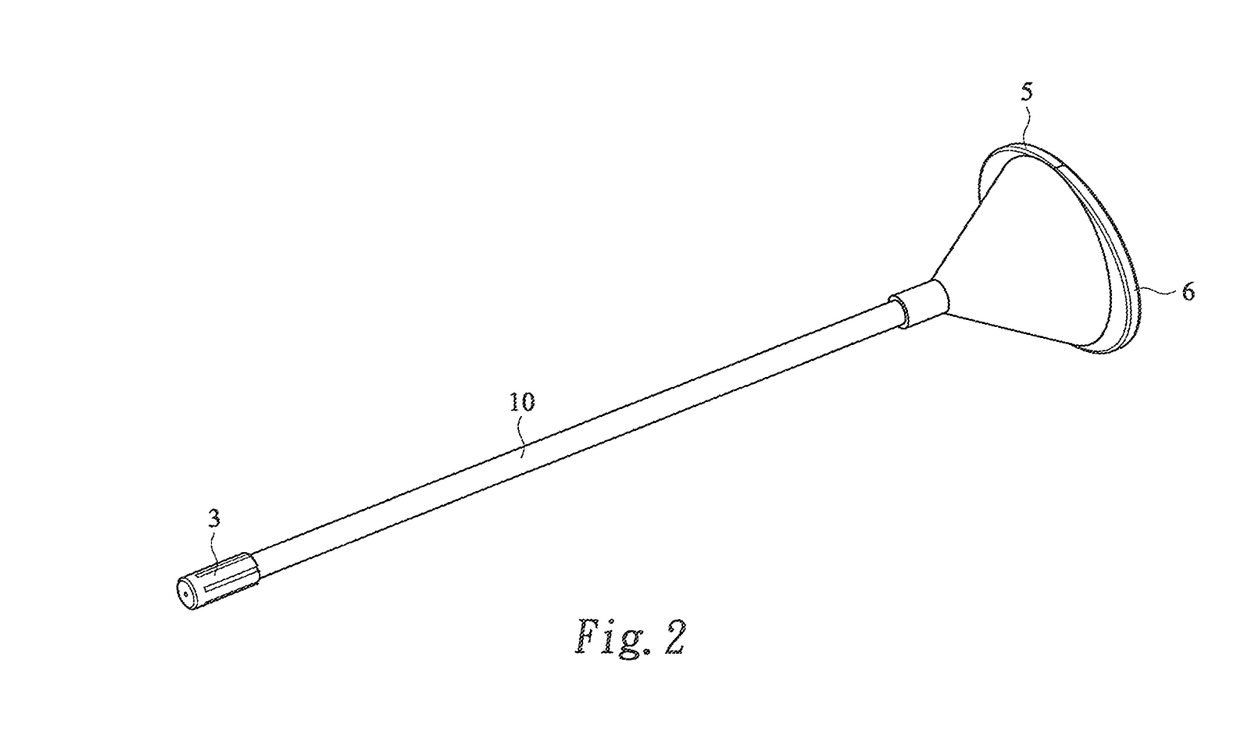
FIG. 2 is a perspective views showing the GDS in FIG. 1 being assembled.

A granule delivery system (hereinafter abbreviated as GDS) constructed according to a first preferred embodiment of the present invention is shown in FIG. 1 and FIG. 2, wherein the GDS comprises a tube 10 having a major portion having a channel 11 of a uniform circular cross section, a first rod 5, a second rod 6 and a perforated cap 3. The tube 10 has a funnel like proximal end to facilitate the filling of porous granules (not shown in FIGS. 1 and 2) into the channel 11 thereof. The perforated cap 3 is used to hold the porous granules having been filled in the channel 11 of the tube 10, and allows the porous granules to be wet by liquid (e.g. blood) through perforations formed on the perforated cap 3. The rod 5 and the rod 6 are identical to each other in this embodiment, each of which has a half circular cross section and a half circular flange at a proximal end thereof, so that they can be joined to form a plunger adapted to be inserted into the tube 10 from the funnel like proximal end thereof by holding the joined half circular flanges. The joined plunger has a cross sectional area about 80-98% of that of the channel 11 of the tube 10. In addition to the half circular cross section and the circular cross section used in this embodiment, other shapes are also possible, which are all shown in FIG. 3 and FIG. 4. A two-step method for delivering the porous granules through the channel 11 of the tube 10 is developed in the present invention, which includes (1) inserting the first rod 5 into the channel 11 from the funnel like proximal end and till another end of the tube 10 to push the porous granules which have been filled in said channel 11, causing a portion of the porous granules to exit from another end of the tube; (2) removing the first rod 5 from the tube 10, joining the first rod 5 and the second rod 6 to form a plunger, and inserting the plunger (the joined first rod 5 and second rod 6) into the channel 11 from the funnel like proximal end of the tube 10 to push the porous granules which remain-in the channel 11 of the tube 10, causing a further portion of the porous granules to exit from the another end of the tube 10. The inserting in the step (2) is stopped when a desired amount of the porous granules exits from the another end of the tube 10, or is all the way till the another end of the tube 10 to empty the tube. Whenever some "resistance" is felt during the step (2) inserting, one can easily go back to the step (1) by pushing only one of the two half rods 5, 6 from there, clear the resistance and then continue the step (2) inserting without pulling out the plunger (the joined first rod 5 and second rod 6). This "resistance clearing" procedure can be carried out repeatedly until all the remaining porous granules are injected.

Figure 5:
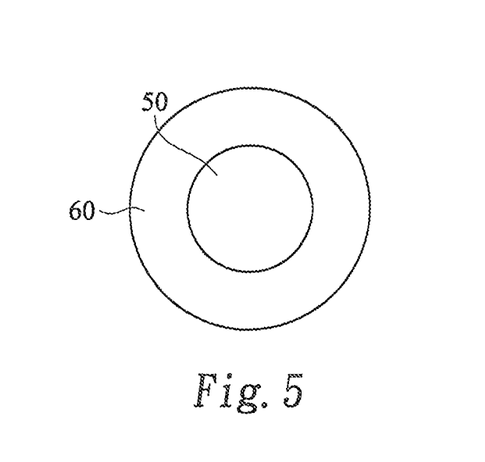
FIG. 5 shows a first rod having a circular cross section and a second rod having an annular cross section for use in the GDS of the present invention.

In addition to the combination of two half circular cross sections used in the first preferred embodiment of the present invention, it is also possible to use a different combination. As shown in FIG. 5, a first rod 50 has a circular cross section and a second rod 60 has an annular cross section having a central hole matching the circular cross section of the first rod 50, so that the first rod 50 and the second rod 60 can be joined to form a plunger having a circular cross section. The first rod 50 and the second rod 60 shown in FIG. 5 can play the same roles as the first rod 5 and the second rod 6 shown in FIG. 1 in the aforesaid two-step method for delivering the porous granules, and the aforesaid "resistance clearing" procedure.

Apparently, the step (2) of the delivery method of the present application can be carried out by using a circular cross sectional plunger corresponding to the joined plunger formed by the first rod 5 (50) and the second rod 6 (60). Alternatively, the circular cross sectional plunger for replacing the joined plunger of the first rod 5 (50) and the second rod 6 (60) in the step (2) may have a cross sectional area which is smaller than that of the joined first rod 5 (50) and second rod 6 (60).

Figure 3:
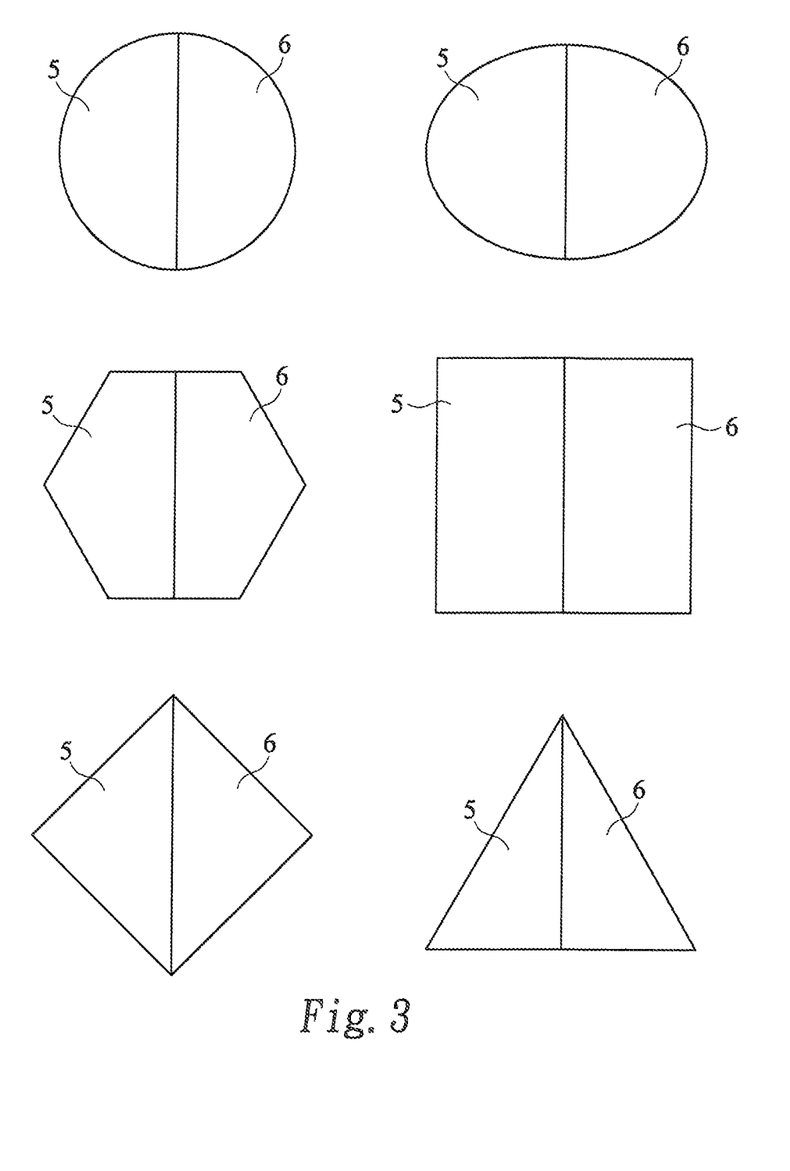
FIG. 3 shows illustrative cross sectional outer profiles of various designs of a first rod and a second rod for use in the GDS of the present invention.
Figure 4:
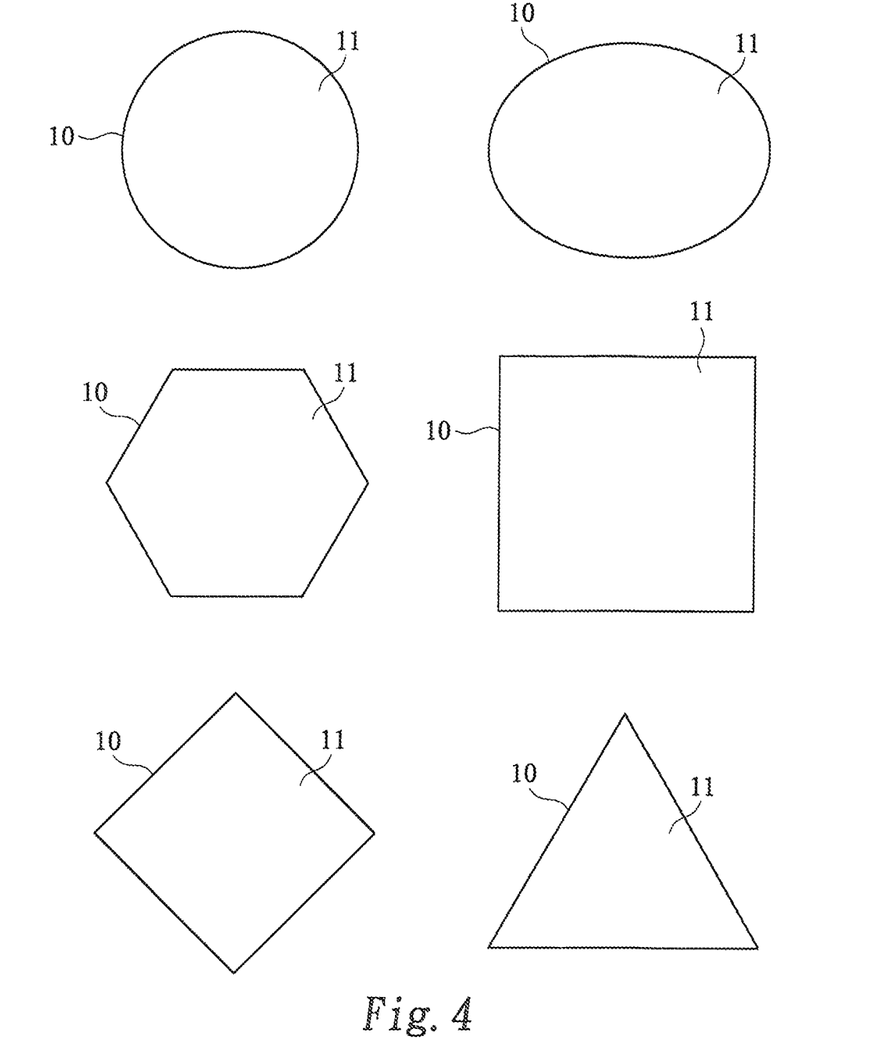
FIG. 4 shows illustrative cross sectional inner profiles of various designs of tubes for use in the GDS of the present invention corresponding to the plungers (rods) shown in FIG. 3.

It is not necessary that the ratio of the cross sectional areas of the first rod to the second rod is about 50%: 50% as shown in FIG. 3. Instead of 50%: 50%, the ratio can be, for examples, 20%: 80%, 30%: 70%, 40%: 60%, 60%: 40%, 70%: 30%, or 80%: 20%. It might be also workable in the delivery method of the present application, when the ratio of the cross sectional areas of the first rod to the second rod is 20%: 70%, 30%: 60%, 40%: 50%, 50%: 40%, 60%: 30%, 70%: 20%, or the like.

Figure 6:
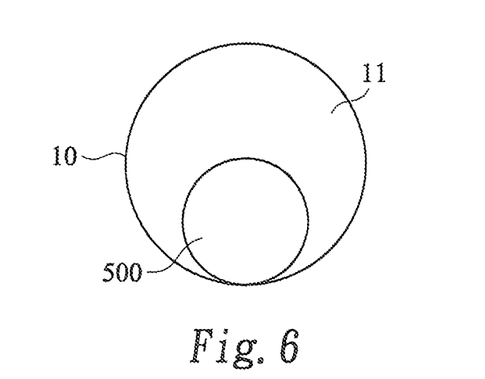
FIG. 6 is an illustrative cross sectional view showing an outer profile of a first rod and an inner profile of a tube of a GDS constructed according to a second preferred embodiment of the present invention in step 1 of a delivery method of the present invention.
Figure 7:
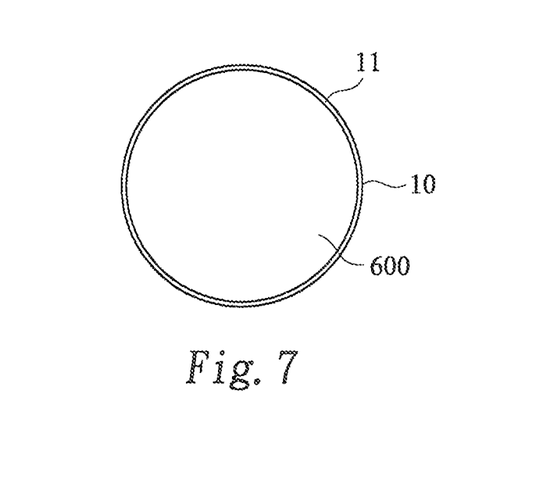
FIG. 7 is an illustrative cross sectional view showing an outer profile of a second rod and an inner profile of a tube of a GDS constructed according to a second preferred embodiment of the present invention in step 1 of the delivery method of the present invention.

A GDS constructed according to a second preferred embodiment of the present invention is similar to the first preferred embodiment of the present invention except the first rod 5 and the second rod 6 shown in FIG. 1 and FIG. 2. In the second preferred embodiment, as shown in FIG. 6 to FIG. 7, a first rod 500 has a circular cross section having a cross sectional area about 30-60% of that of the channel 11 of the tube 10, and a second rod 600 has a circular cross section having a cross sectional area about 80-98% of that of the channel 11 of the tube 10. The delivery method of the present invention is carried out by using the first rod 500 in the above-mentioned step (1) and using the second rod 600 in the above-mentioned step (2).

Figure 8:
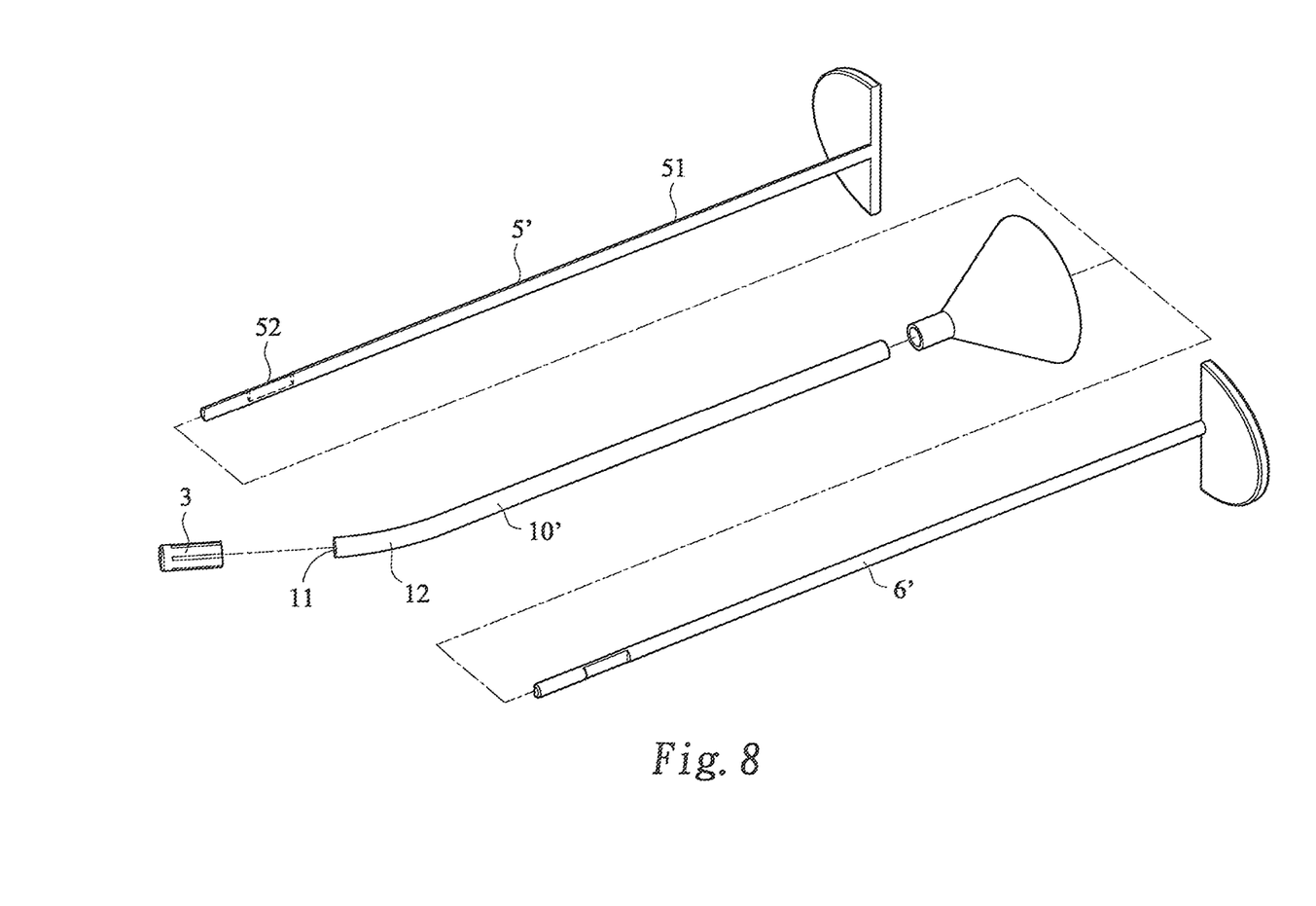
FIG. 8 is a perspective view showing a granule delivery system constructed according to a third preferred embodiment of the present invention.

A GDS constructed according to a third preferred embodiment of the present invention is similar to the first preferred embodiment of the present invention shown in FIG. 1 and FIG. 2; however, the distal end of the GDS is curved so that it is adapted to reach a site which cannot be or is difficult to be reached linearly. In the third preferred embodiment, as shown in FIG. 8, the GDS has a tube 10' having a curved section 12 at a distal end thereof; a first rod 5' having a half circular cross section 51 having a cross sectional area about 50% of that of a channel 11 of the tube 10', and a thinner section 52 having a reduced cross-sectional area in comparison with that of the section 51; and a second rod 6' identical to the first rod 5'. The thinner section 52 has a strength enough to allow the first rod 5' to push the porous granules filled in the channel 11 of the tube 10', and a flexibility to allow a distal end of the first rod 5' to enter the curved section 12 of the tube 10'. The delivery method of the present invention is carried out by using the first rod 5' in the above-mentioned step (1) and using a joined plunger formed by the first rod 5' and the second rod 6' in the above-mentioned step (2).

Apparently, the step (2) of the delivery method of the present application can be carried out by using a single plunger having a structure corresponding to the joined plunger formed by the first rod 5' and the rod 6'.

Example 1: Plastic Tubes and Plungers Made by Rapid Prototyping (RP)

In this example the tubes and the plungers were made of plastic material by rapid prototyping (RP).
Comparative One-Step Method Porous granules having sizes between 0.8 to 0.42 mm filled in a thin tube having a length and an inner diameter as shown in Table 1. The weights of the filled tube and the empty tube were measured, so that the weight of the porous granules filled in the tube could be calculated (W0). The porous granules were then wet with water, and were pushed by a circular plunger having a length longer that of the tube and a diameter matches the inner diameter of the tube. The wet granules exited from the tube were dried by baking, gently broken into granules, and screened to obtain granules having a size less than 0.42 mm, which was weighed (W1). The percentage of (W0-W1)/W0 was calculated and listed in Table 1 as the granule delivery yield.
Two-Step Method Porous granules having sizes between 0.8 to 0.42 mm filled in a thin tube having a length and an inner diameter as shown in Table 1. The weights of the filled tube and the empty tube were measured, so that the weight of the porous granules filled in the tube could be calculated (W0). The porous granules were then wet with water, and were pushed by a first rod, and a second rod after removing the first rod from the tube. The shapes of the cross sections of the first rod and the second rod are both circular; however, the cross sectional area of the first rod is smaller than that of the second rod which has a diameter matching the inner diameter of the tube, as listed in Table 1. The wet granules exited from the tube were dried by baking, gently broken into granules, and screened to obtain granules having a size less than 0.42 mm, which was weighed (W1). The percentage of (W0-W1)/W0 was calculated and listed in Table 1 as the granule delivery yield.

TABLE 1

| Delivery method | Tube length (mm) | Tube inner dia. (mm) | $1^{st}$ plunger cross-section area (mm$^2$) ($1^{st}$ step insertion) | $2^{nd}$ plunger cross-section area (mm$^2$) ($2^{nd}$ step insertion) | Granule delivery yield (%) |
|---|---|---|---|---|---|
| One step (conventional one plastic plunger | 180 | 5.0 | 19.6 | — | 39 |
| One step (conventional one plastic plunger) | 180 | 4.0 | 12.6 | — | 32 |
| One step (conventional one plastic plunger) | 180 | 3.0 | 7.1 | — | 0 |
| One step (conventional one plastic plunger) | 180 | 2.5 | 4.9 | — | 0 |
| Two-step (two round plastic plungers) | 180 | 3.0 | 4.9 | 7.1 | 10 |
| Two-step (two round plastic plungers) | 180 | 3.0 | 3.1 | 7.1 | 12 |
| Two-step (two round plastic plungers) | 180 | 3.0 | 0.8 | 7.1 | 15 |
| Two-step (two round plastic plungers) | 180 | 2.5 | 3.1 | 4.9 | 23 |

The results shown in Table 1 indicate that the conventional one-step method is difficult or impossible to deliver the porous granules through tubes having a length of 180 mm and an inner diameter of 5 mm or less. By using the two-step method of the present invention with the first thinner plunger and the second matching plunger, it becomes possible to deliver the porous granules through tubes having a length of 180 mm and an inner diameter of 3 mm or 2.5 mm.

Example 2: 316 Stainless Steel Tubes and Plungers

In this example the tubes and the plungers were made of 316 stainless steel.

Porous granules having sizes between 0.8 to 0.42 mm filled in a thin tube having a length and an inner diameter as shown in Table 2. The weights of the filled tube and the empty tube were measured, so that the weight of the porous granules filled in the tube could be calculated (W0). The porous granules were then wet with water, and were pushed by a first rod ($1^{st}$ plunger). A second rod identical to the first rod was joined with the first rod after removing the first rod from the tube, and then the joined first rod and second rod ($2^{nd}$ plunger) was inserted into the tube to push the porous granules remaining in the tube. The wet granules exited from the tube were dried by baking, gently broken into granules, and screened to obtain granules having a size less than 0.42 mm, which was weighed (W1). The percentage of (W0-W1)/W0 was calculated and listed in Table 2 as the granule delivery yield.

TABLE 2

| Delivery method | Tube length (mm) | Tube inner dia. (mm) | $1^{st}$ plunger cross-section area (mm$^2$) ($1^{st}$ step insertion) | $2^{nd}$ plunger cross-section area (mm$^2$) | $1^{st}$ plunger/ $2^{nd}$ plunger combination cross-section area (mm$^2$) ($2^{nd}$ step insertion) | Granule delivery yield (%) |
|---|---|---|---|---|---|---|
| One-step (conventional one circular steel plunger) | 200 | 3.0 | 7.1 | — | — | 0 |
| One-step (conventional one circular steel plunger) | 200 | 4.0 | 12.6 | — | — | 31.1 |
| One-step (conventional one circular steel plunger) | 200 | 5.0 | 19.6 | — | — | 39.6 |
| Two-step (two semi-circular steel plungers) | 200 | 3.0 | 3.55 | 3.55 | 7.1 | 63.4 |
| Two-step (two semi-circular steel plungers) | 200 | 4.0 | 6.3 | 6.3 | 12.6 | 65.7 |
| Two-step (two semi-circular steel plungers) | 200 | 5.0 | 9.8 | 9.8 | 19.6 | 95.3 |

The results shown in Table 1 and Table 2 indicate that the 316 stainless steel can provide a better delivery yield in comparison with the RP plastic material as evidenced by the runs using tubes having an inner diameter of 3 mm. The results in Table 2 also show that the delivery yield is satisfactory by using the two-step method of the present invention with the two semi-circular rods to deliver the porous granules through tubes having a length of 200 mm and an inner diameter of 3.0 mm, and is as high as 95.3% when the inner diameter is 5.0 mm.

The invention claimed is:

1. A method for delivering porous particulate material through a tube comprising a major section having a channel of a uniform cross section, said method comprising filling the porous particulate material in said tube; inserting a first rod into said channel from one end of said tube to push said porous particulate material filled in said channel, causing a portion of said porous particulate material to exit from another end of said tube, wherein said first rod has a cross sectional area which is 20-50% of that of said channel, and said method further comprising withdrawing said first rod from said tube; and inserting said first rod into said channel again to push said porous particulate material remains in said channel, causing a further portion of said porous particulate material to exit from said another end of said tube; and optionally repeating said withdrawing and said inserting to cause more said porous particulate material to exit from said another end of said tube.

2. A method for delivering particulate material through a tube comprising a major section having a channel of a uniform cross section, said method comprising filling the particulate material in said tube; inserting a first rod into said channel from one end of said tube to push said particulate material filled in said channel, causing a portion of said particulate material to exit from another end of said tube, wherein said first rod has a cross sectional area which is 20-50% of that of said channel, and said method further comprising removing said first rod from said tube; and inserting a second rod into said channel from said one end of said tube to push said particulate material which remains in said channel, causing a further portion of said particulate material to exit from said another end of said tube, wherein said second rod has a cross sectional area which is 80-100% of that of said channel.

3. The method of claim 2, wherein said particulate material is porous particulate material.

4. A method for delivering particulate material through a tube comprising a major section having a channel of a uniform cross section, said method comprising filling the particulate material in said tube; inserting a first rod into said channel from one end of said tube to push said particulate material filled in said channel, causing a portion of said particulate material to exit from another end of said tube, removing said first rod from said tube; and inserting a second rod into said channel from said one end of said tube to push said particulate material which remains in said channel, causing a further portion of said particulate material to exit from said another end of said tube, wherein each of the first rod and the second rod has a cross sectional area of 30-70% of a cross sectional area of said channel, and a combined cross sectional area of the first rod and the second rod is less than or equal to the cross sectional area of said channel, wherein the first rod is joined to the second rod after the first rod being removed from said tube, and the second rod with the first rod joined thereto is inserted into said channel from said one end of said tube, wherein the first rod and the second rod cross sectional area are about 50% of the cross sectional area of said channel, and the combined cross sectional area of the first rod and the second rod is about equal to the cross sectional area of said channel.

5. The method of claim 4, wherein said particulate material is porous particulate material.

* * * * *